United States Patent
Hortobágyi et al.

(10) Patent No.: US 10,421,737 B2
(45) Date of Patent: Sep. 24, 2019

(54) PROCESS FOR THE PREPARATION OF OPTICALLY ACTIVE BERAPROST

(71) Applicant: CHINOIN GYÓGYSZER ÉS VEGYÉSZETI TERMÉKEK GYÁRA ZRT., Budapest (HU)

(72) Inventors: Irén Hortobágyi, Budapest (HU); István Lászlófi, Budapest (HU); Zsuzsanna Kardos, Budapest (HU); József Molnár, Budapest (HU); László Takács, Budapest (HU); Tamás Bán, Budapest (HU)

(73) Assignee: CHINOIN PHARMACEUTICAL AND CHEMICAL WORKS PRIVATE COMPANY LTD., Budapest (HU)

( * ) Notice: Subject to any disclaimer, the term of this patent is extended or adjusted under 35 U.S.C. 154(b) by 0 days.

(21) Appl. No.: 16/091,019

(22) PCT Filed: Mar. 30, 2017

(86) PCT No.: PCT/EP2017/057582
§ 371 (c)(1),
(2) Date: Oct. 3, 2018

(87) PCT Pub. No.: WO2017/174439
PCT Pub. Date: Oct. 12, 2017

(65) Prior Publication Data
US 2019/0062295 A1  Feb. 28, 2019

(30) Foreign Application Priority Data
Apr. 5, 2016 (HU) .................... 1600232

(51) Int. Cl.
C07D 307/93 (2006.01)
(52) U.S. Cl.
CPC ........ *C07D 307/93* (2013.01); *C07B 2200/07* (2013.01); *C07B 2200/13* (2013.01)
(58) Field of Classification Search
USPC ....................................................... 549/458
See application file for complete search history.

(56) References Cited

U.S. PATENT DOCUMENTS

| | | | | |
|---|---|---|---|---|
| 8,183,286 B2 * | 5/2012 | Faulds | ............... | A61K 31/5575 514/470 |
| 2004/0209945 A1 * | 10/2004 | Szabo | ............... | C07D 307/93 514/468 |
| 2012/0323025 A1 * | 12/2012 | Sharma | ............... | C07D 307/93 549/458 |
| 2014/0288314 A1 | 9/2014 | Batra et al. | | |

FOREIGN PATENT DOCUMENTS

| WO | WO 03/011849 A1 | 2/2003 |
|---|---|---|
| WO | WO 2012/174407 A1 | 12/2012 |

OTHER PUBLICATIONS

Hungarian Search Report dated Oct. 10, 2016, for Hungarian Application No. 1600232, with an English translation.
International Search Report (form PCT/ISA/210) for International Application No. PCT/EP2017/057582 dated May 11, 2017.
Smith et al., "March's Advanced Organic Chemistry: Reactions, Mechanisms, and Structure", 6th Edition, 2007, pp. 173-175 (7 pages total).
Wakita et al., "Synthesis of 5,6,7-Trinor-4,8-Inter-m-Phenylene $PGI_2$ and Beraprost", Tetrahedron, vol. 55, 1999, pp. 2449-2474.
Wakita et al., "Total Synthesis of Optically Active m-Phenylene $PGI_2$ Derivative: Beraprost", Heterocycles, vol. 53, No. 5, 2000, pp. 1085-1110 (26 pages total).
Written Opinion of the International Searching Authority (Form PCT/ISA/237) for International Application No. PCT/EP2017/057582, dated May 11, 2017.

* cited by examiner

*Primary Examiner* — Taofiq A Solola
(74) *Attorney, Agent, or Firm* — Birch, Stewart, Kolasch & Birch, LLP

(57) ABSTRACT

The invention provides a new process for the preparation of optically active Beraprost of formula (I) starting from racemic Beraprost alkyl ester through hydrolysis, enantiomer esterification, preparation of diacyl-Beraprost ester diastereomers and their separation and hydrolysis.

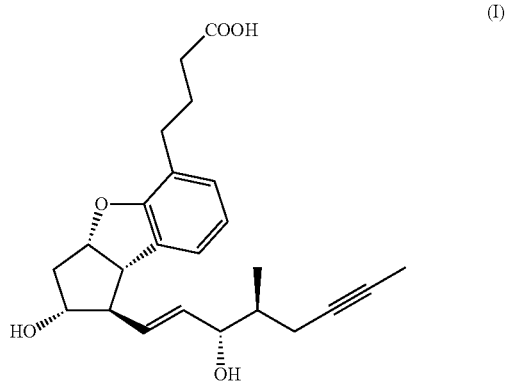

(I)

17 Claims, 2 Drawing Sheets

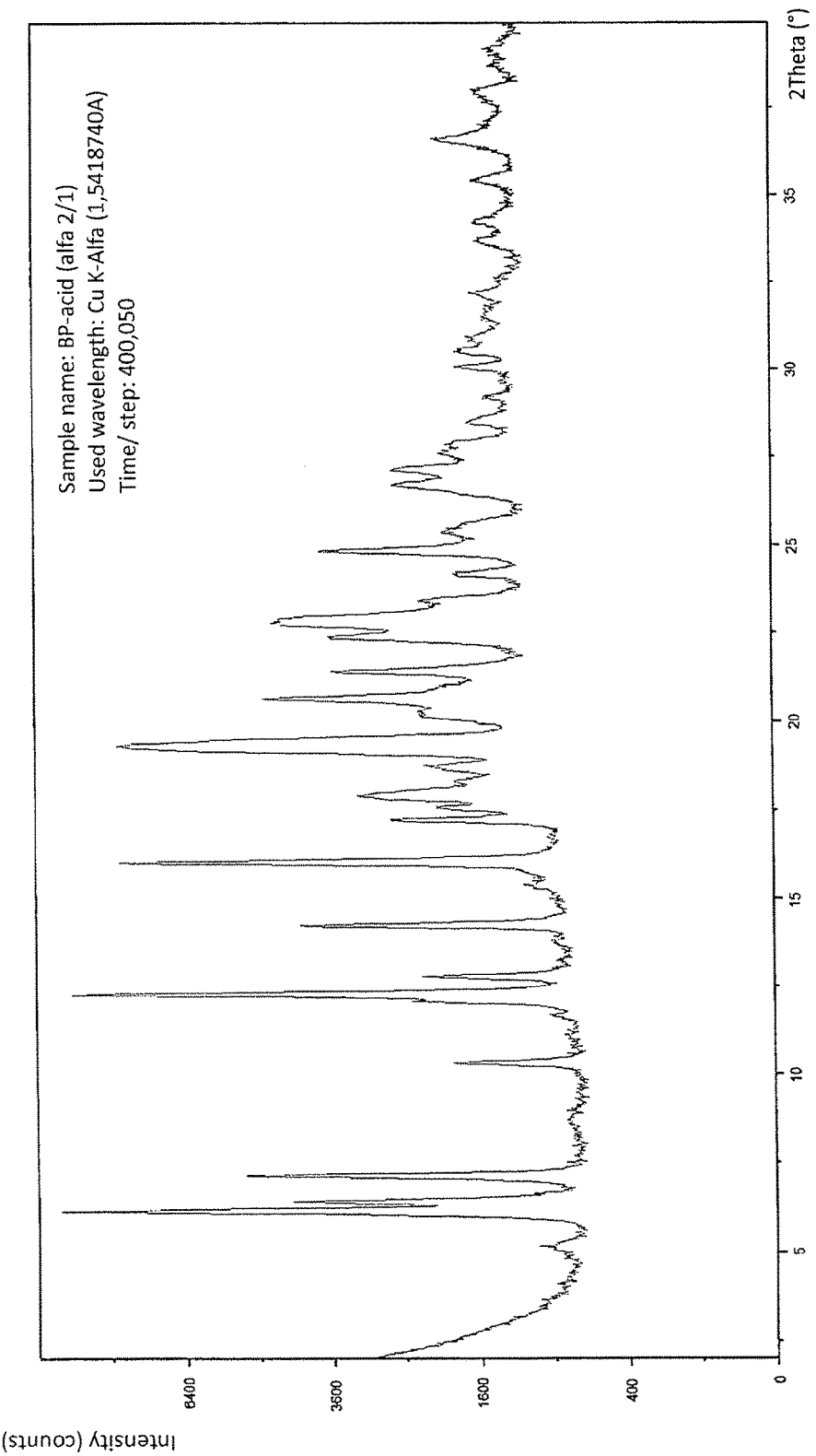

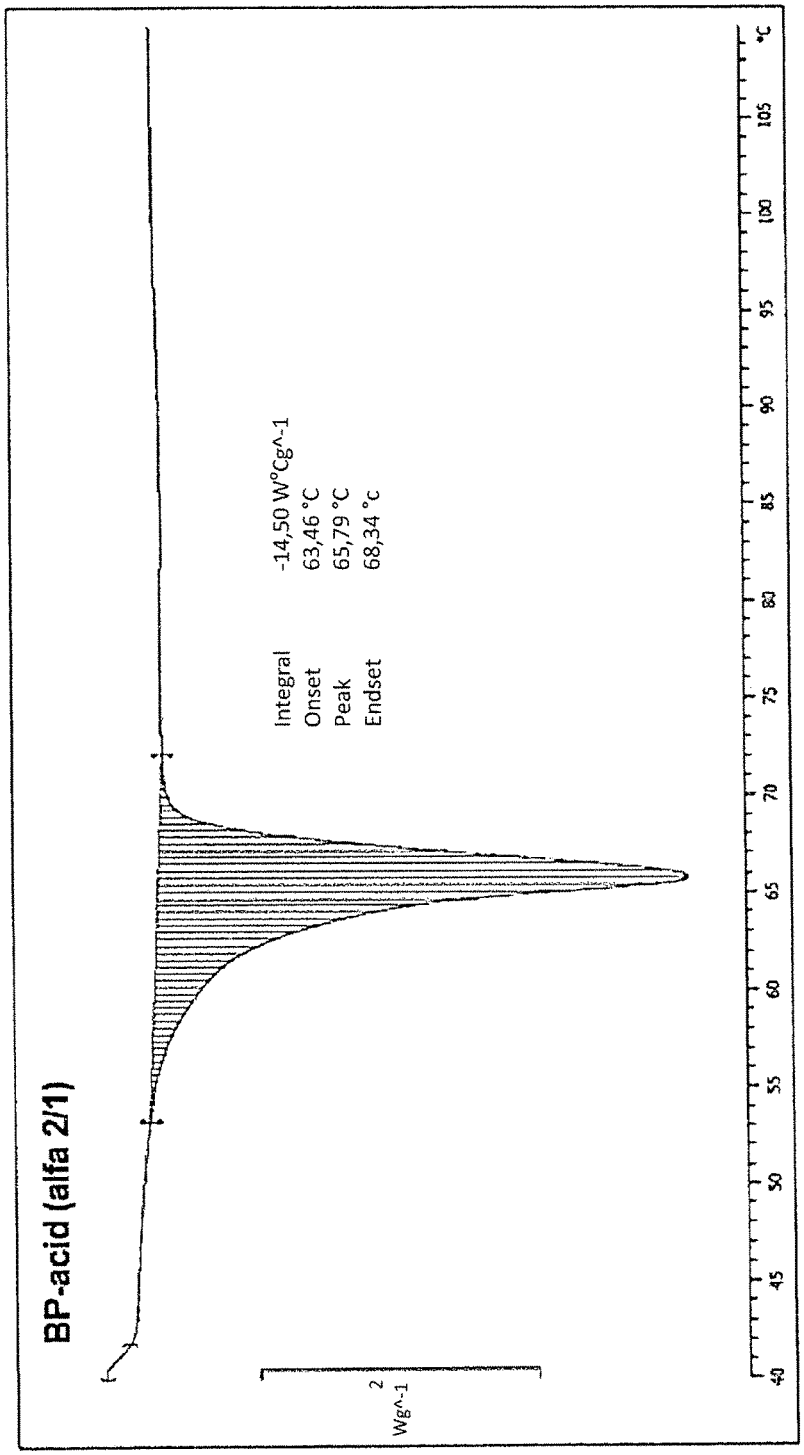
DSC curve
(Continued)

PROCESS FOR THE PREPARATION OF OPTICALLY ACTIVE BERAPROST

The subject of the invention of the present patent application is a process for the preparation of optically active (1 alpha 2/1) Beraprost of formula I and its salts

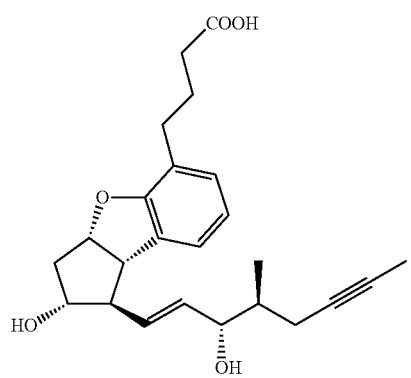

The commercially available Beraprost sodium is used for the treatment of peripheral arterial diseases (*Drugs*, 2002, 62, 107-133), and since 2007 it is also used for the treatment of pulmonary arterial hypertonia (PAH) (*J. Am. Coll. Cardiol.*, 2004, 43, 56S-61S).

Considering its chemical structure Beraprost Na is a racemic compound, the mixture of four isomers.

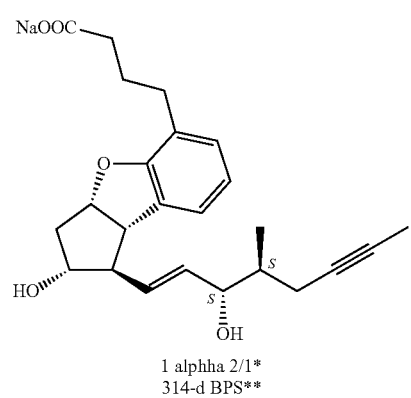

1 alphha 2/1*
314-d BPS**

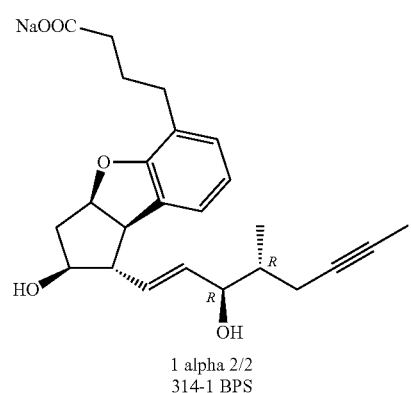

1 alpha 2/2
314-1 BPS

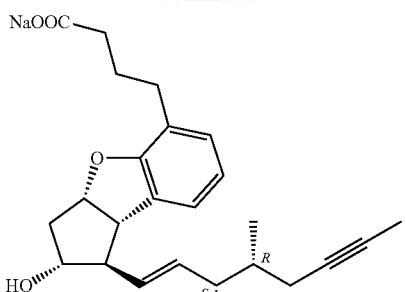

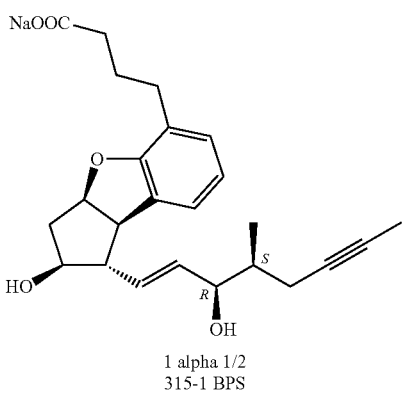

1 alpha 1/1
315-d BPS 1 alpha 1/2
315-1 BPS

*CHINOIN denomination, **Toray denomination (also published in CAS)

The starting material of the Beraprost synthesis of Toray company is cyclopentadiene (2). Cyclopentadiene was brominated, the dibromocyclopentene (3) was reacted with tribromophenol. The Grignard reagent formed from the obtained compound was converted in the presence of CuI catalyst into the racemic tricycle (rac-5)*, from which by Prins reaction the racemic dihydroxy derivative (rac-6) was prepared. The two hydroxy groups were protected through the acetal (rac-7), the upper chain was built via formylpropionic acid methyl ester (8) and hydrogenation, the acetal protecting group was cleaved, the two hydroxyl groups were selectively protected, the primary hydroxyl group was liberated and oxidized to the aldehyde (rac-9). The lower chain was built by Horner-Wadsworth-Emmon (HWE) reaction by using racemic phosphonate (10), the keto group of the resulting racemic enone derivative (rac-11) was reduced to hydroxyl group, the isomers were separated (rac-12), the ester groups were hydrolysed and the sodium salt of the acid was isolated (*Tetrahedron*, 1999, 55, 2449-2474). (Schema 1.).

Schema 1.

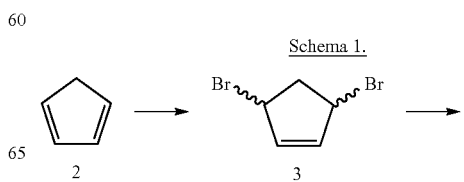

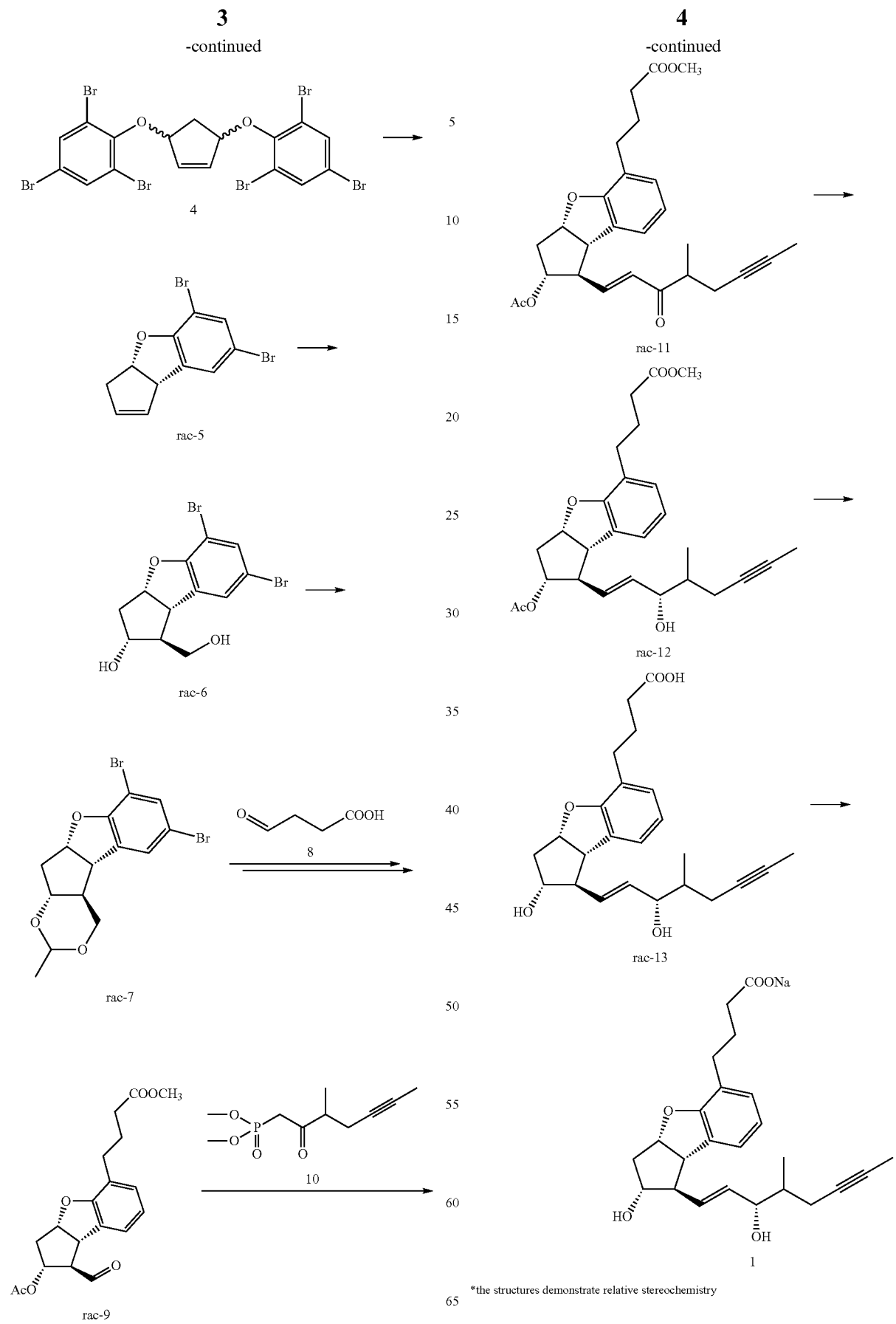
*the structures demonstrate relative stereochemistry

For application in further therapeutic fields it became necessary that the most effective form, the active Beraprost (314-d BPS=1alpha 2/1) be available in optically pure form.

According to the process published by Toray company the optically active Beraprost Na (1 alpha2/1) was prepared by reacting the Grignard reagent obtained from the racemic tricycle (rac-5) with carbon dioxide and by resolution of the obtained crude racemic acid with the chiral amine ((+)-cis-N-benzyl-2-(hydroxymethyl)cyclohexylamine) to obtain the optically active acid (14) (*Tetrahedron Asymmetry*, 1999, 10, 4099-4105).

Onto the double bond of the optically active acid (14) the hydroxy- and hydroxymethyl-groups were formed by Prins reaction, the bromo group was removed by catalytic hydrogenation, the acid function was esterified (15), the free hydroxy groups were protected with THP groups, the ester group was reduced to alcohol and then oxidized to aldehyde (16), the upper chain was built by Wittig reaction, the acid was transformed to the methyl ester, the THP groups were then removed (17), the double bond in the upper chain was saturated, the hydroxy groups were selectively protected, the primary hydroxy group was liberated and then oxidized to the aldehyde to obtain the optically active form (9) of rac-9. The aldehyde was reacted with the chiral phosphonate (S-10), which through the already described chemical steps was converted into the optically active Beraprost Na isomer. All four Beraprost Na isomers were prepared, but the publication discloses neither the preparation of the salts nor the characteristics of the salts (*Heterocycles*, 2000, 53, 1085-1110). (Schema 2.)

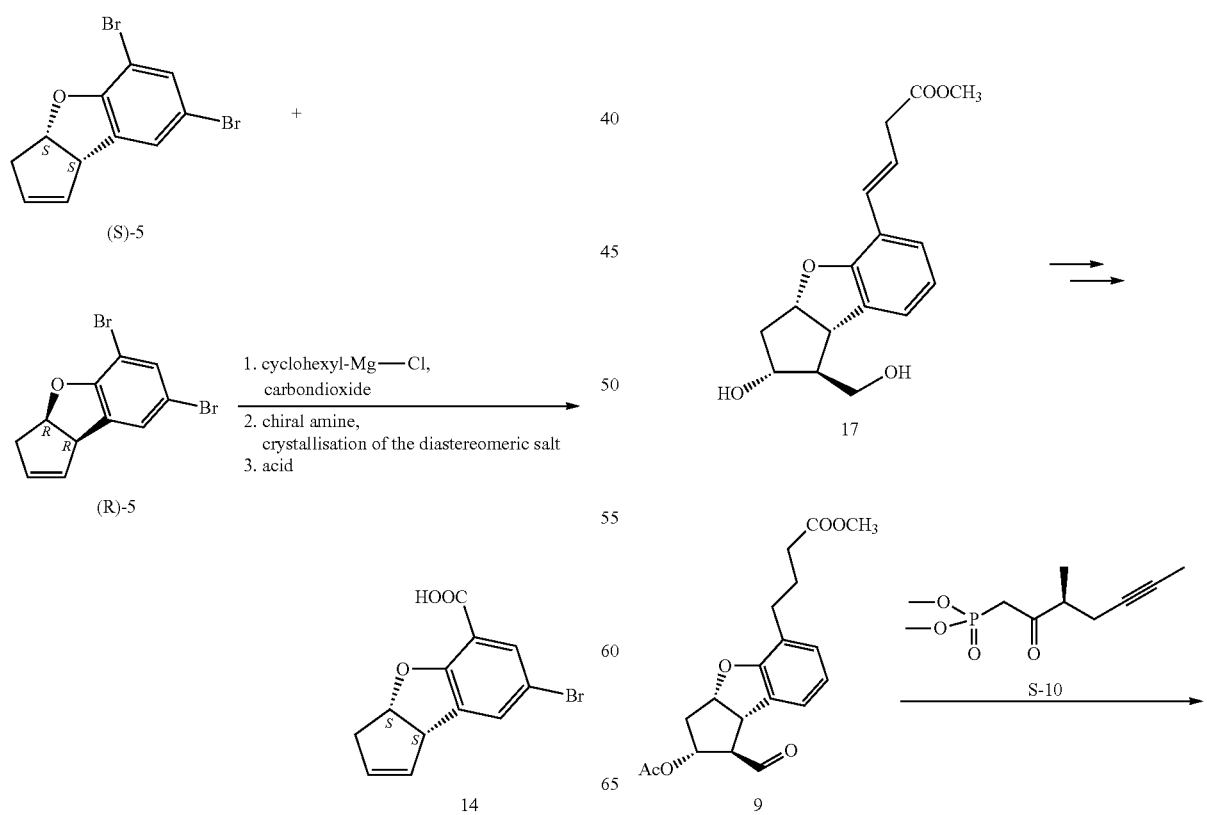

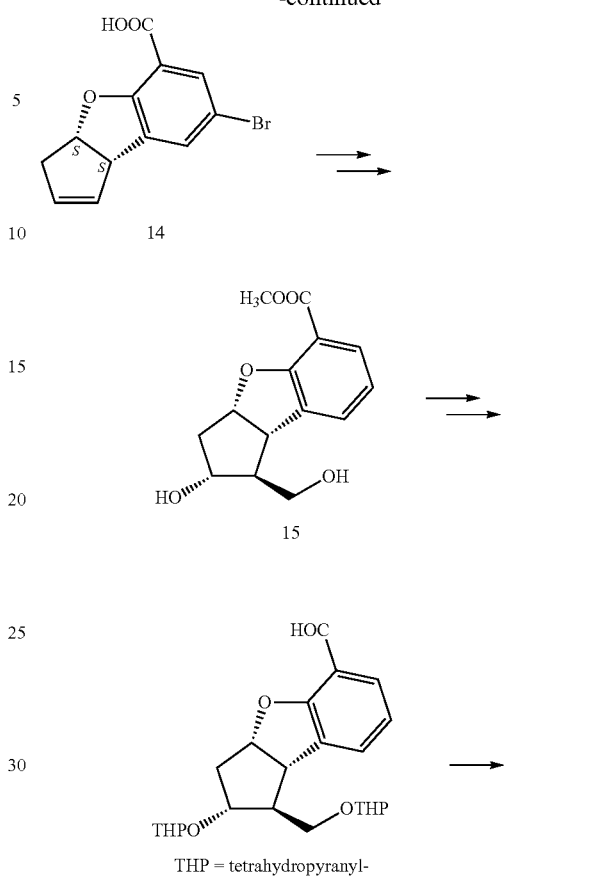

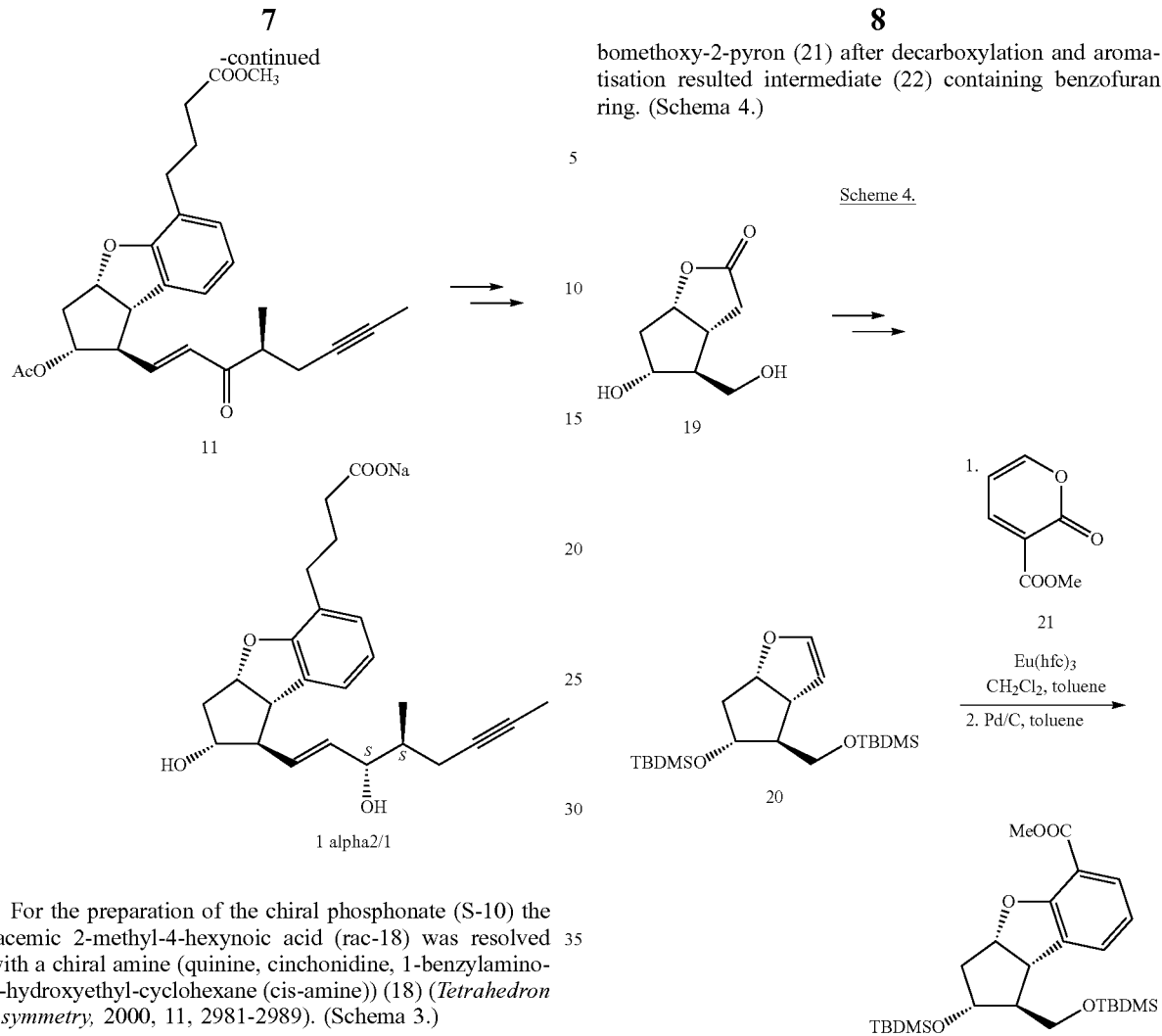

bomethoxy-2-pyron (21) after decarboxylation and aromatisation resulted intermediate (22) containing benzofuran ring. (Schema 4.)

For the preparation of the chiral phosphonate (S-10) the racemic 2-methyl-4-hexynoic acid (rac-18) was resolved with a chiral amine (quinine, cinchonidine, 1-benzylamino-2-hydroxyethyl-cyclohexane (cis-amine)) (18) (*Tetrahedron Asymmetry*, 2000, 11, 2981-2989). (Schema 3.)

TBDMS = tert-butyl-dimethylsilyl-

To build the upper chain the methyl ester group of 22 was transformed in two steps into the aldehyde, from the aldehyde (23) with dimethyl-(1-diazo-2-oxopropyl)-phosphonate (24) the acetylene derivative (25) was gained, which was reacted with ethyl-diazoacetate (26), and finally the triple-bond was saturated by catalytic hydrogenation (27). (Schema 5.)

Patent application WO 2012/174407 A1 discloses the preparation of the optically active Beraprost. Starting material of the synthesis is the optically active Corey-lactone (19), which was transformed in several steps into the protected dihydrofuran derivative (20). Lantanida-catalyzed (Eu(hfc)₃) Diels-Alder reaction of 20 with the 3-car-

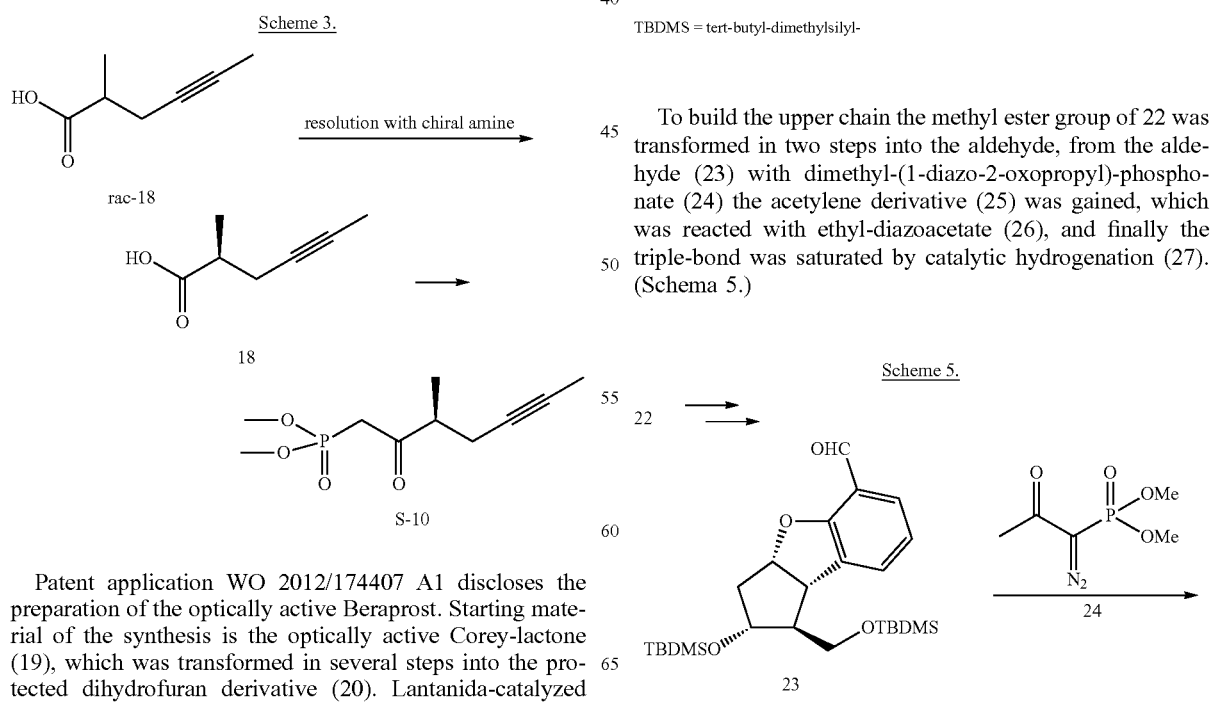

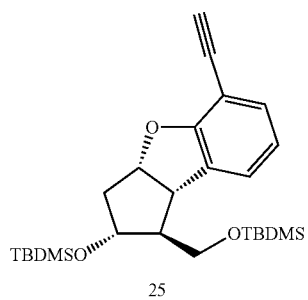

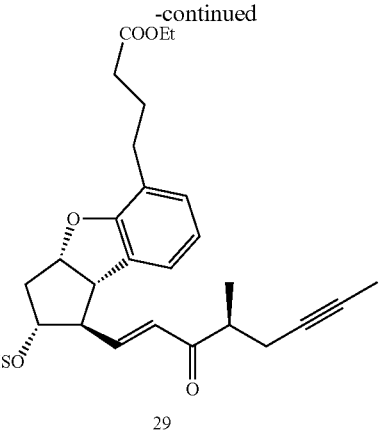

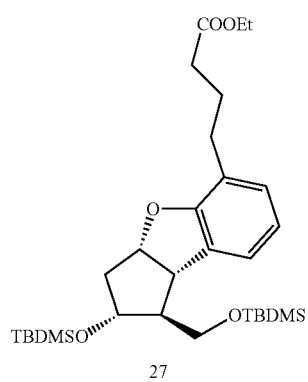

The primary hydroxyl group of the protected diol 27 was liberated and oxidized into the aldehyde, the aldehyde 28 was reacted with the S-10 phosphonate, the oxo group of the enone 29 was reduced with sodium borohydride cerium(III) chloride reagent, or with selective reduction in the presence of (R)-(+)-CBS catalyst with catecholborane or boran-dimethylsulfide reagent to obtain (30), from the secondary alcohol the protecting group was removed, the ester was transformed with sodium hydroxide in methanol solution into the sodium salt (Schema 6.)

Schema 6.

27 ⟶

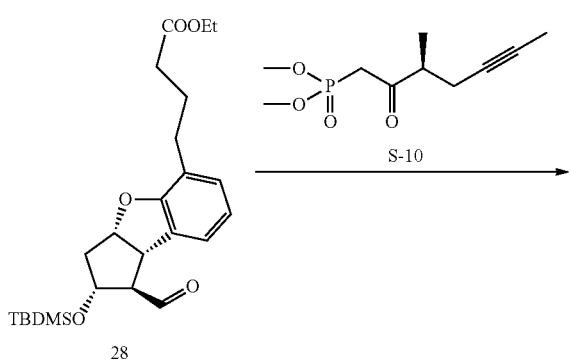

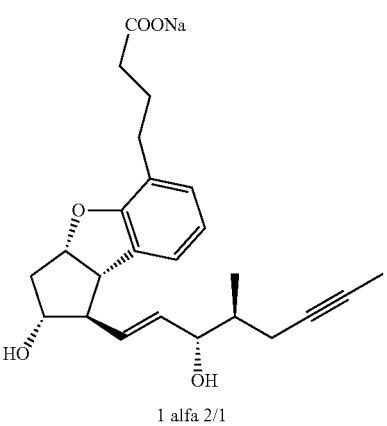

1 alfa 2/1

Physical characteristics of the sodium salt have not been disclosed.

From the active Beraprost acid the potassium salt was also been prepared, in ethyl acetate with potassium hydroxide in ethanol. The potassium salt was recrystallized from aqueous ethanol.

The Starting material of the process disclosed in patent application WO 2013/040068 A1 is the optically active cyclopentenone derivative 31, which was alkylated with the bromophenol derivative 32. The aryl ether 33 was cyclized, the oxo-group was reduced to obtain the alcohol (34). The secondary hydroxyl group was protected with acetyl group and PdCl$_2$-catalyzed oxidative transformation of the double bond resulted derivative 35. By ozonolysis of the double bond followed by reaction with triphenylphosphine the aldehyde 9 was obtained (Schema 7.)

Schema 7.

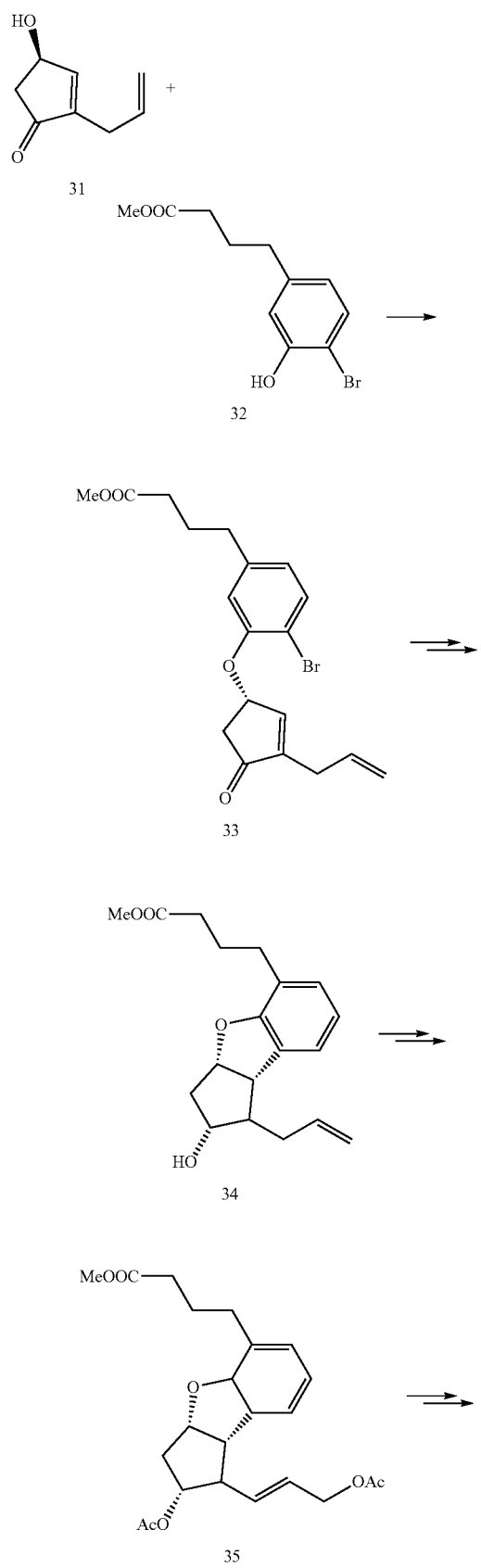

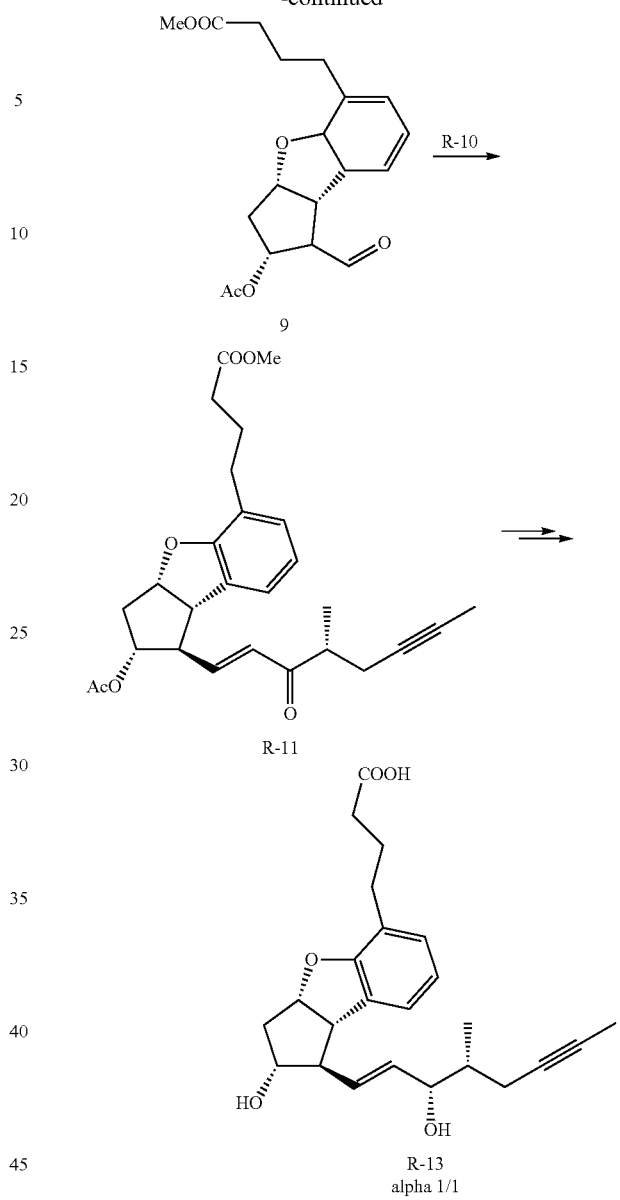

The aldehyde 9 was reacted with the optically active R-10 phosphonate, the oxo group of the enone R-11 was selectively reduced with borane-tetrahydrofuran reagent in the presence of (R)-CBS catalyst, the ester groups were then hydrolyzed to obtain the alpha 1/1 isomer of Beraprost acid, which is not the active isomer.

The patent claims the preparation of each Beraprost acid isomers via the above chemical steps by using the respective phosphonate enantiomers (S-10 and R-10).

Preparation of Beraprost Na salts is not described in the specification.

Starting material of the process according to patent specification WO2015/179427 is the chiral halogen derivative 35, which was transformed in several steps into the protected diol 36. The free hydroxyl group of the diol 36 was oxidized to obtain the aldehyde, the aldehyde was then reacted with the chiral phosphonate S-10.

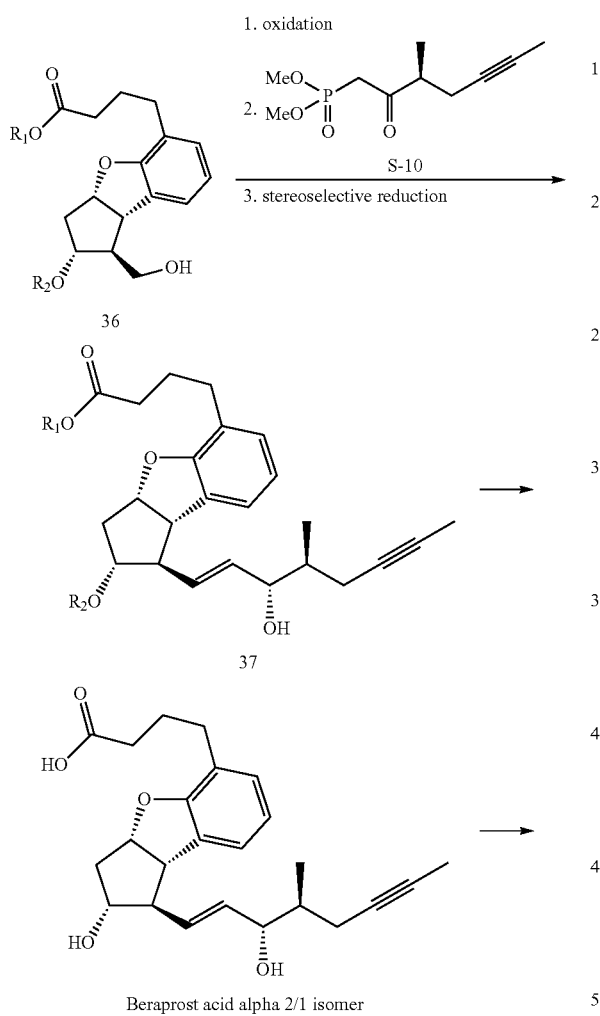

$R_1$ = methyl- or ethyl-
$R_2$ = H or a group suitable for the protection of alcohols The stereoselective reduction was also performed in the case of $R_2$=H and $R_2$=tert.-butyl-dimethylsilyl. The active ester 37 was hydrolyzed to the acid. The acid (solid foam) was transformed into the crystalline potassium salt.

The subject of our invention is process for the preparation of the optically active Beraprost of formula I and its salts,

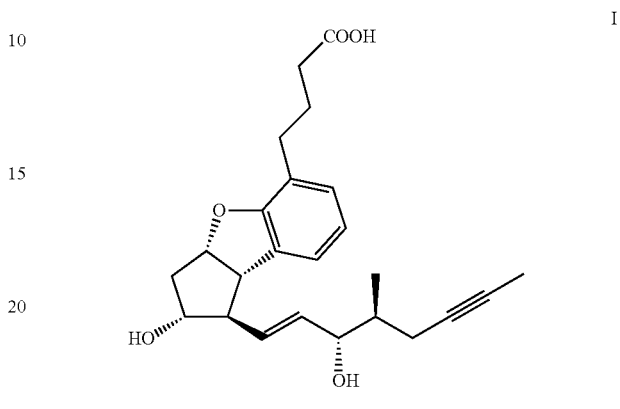

characterized by, that
a racemic Beraprost ester of the general formula II,

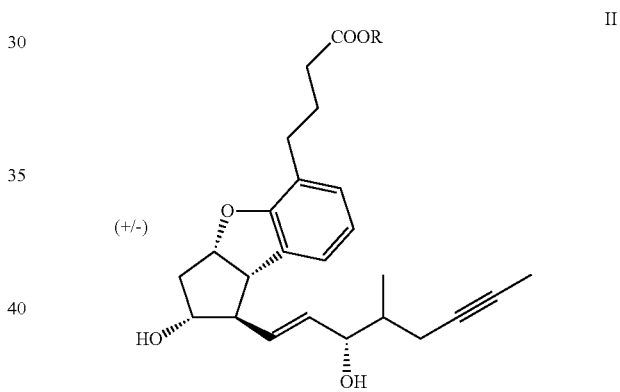

where R stands for a $C_{1-4}$ straight- or branched-chain alkyl group, is hydrolyzed, the resulting racemic Beraprost acid of formula III

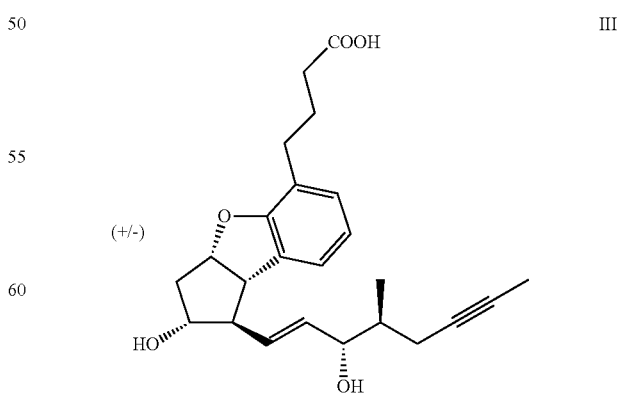

is crystallized, the obtained Beraprost acid enantiomers of formulae IIIa and IIIb are

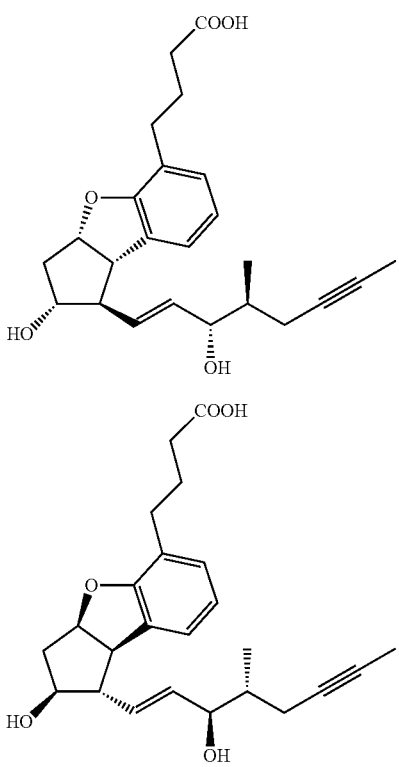

esterified, the obtained Beraprost ester enantiomers IVa and IVb,

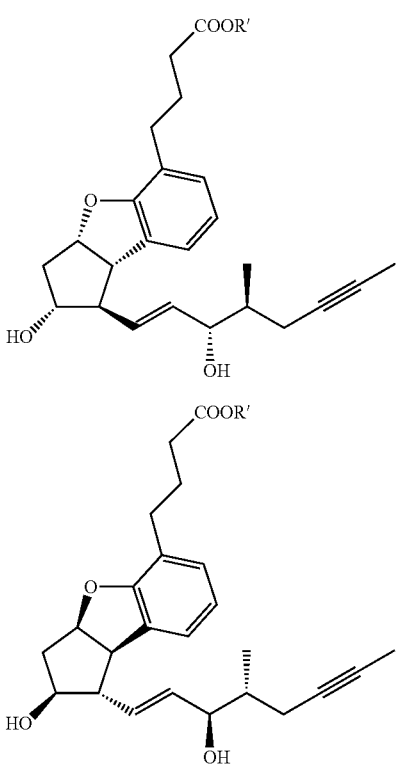

where R' stands for $C_{1-4}$ straight- or branched-chain alkyl group, are reacted with chiral acid or acid derivative, the obtained diacyl-Beraprost ester diastereomers VIa and VIb,

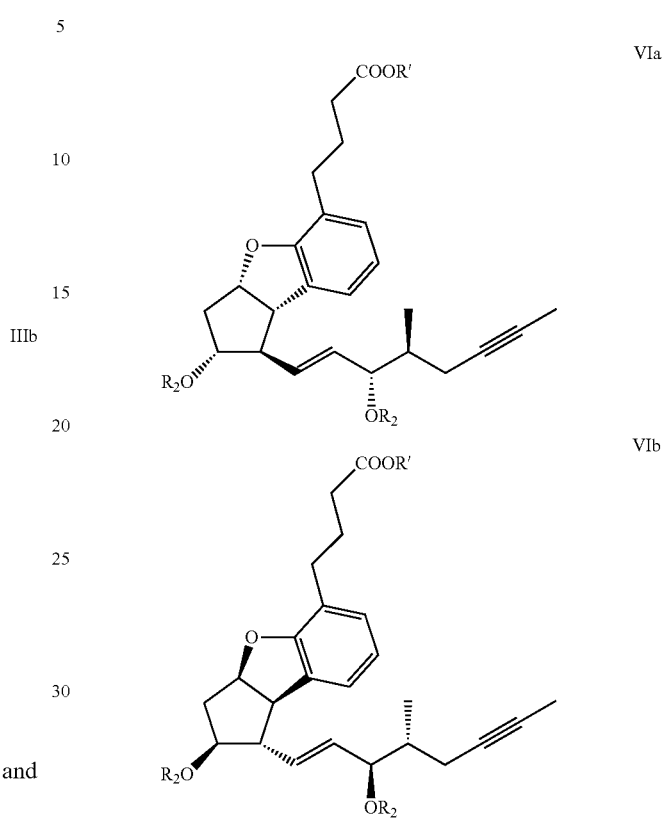

where R' has the same meaning as above, and $R_2$ means an acid residue containing chiral carbon atom, are separated, the Beraprost ester of formula VIa is hydrolyzed and the obtained optically active Beraprost acid of formula I is isolated in crystalline form, if desired, transformed into its salt.

BRIEF DESCRIPTION OF THE DRAWINGS

FIG. 1 shows the characteristic peaks of the X-ray diffraction spectrum of the optically active Beraprost acid of the present invention.

According to a preferred embodiment of the invention hydrolysis of the compound of formula II is carried out in a water-miscible organic solvent with the aqueous solution of an inorganic base, as solvents alcohols, methanol, ethanol, isopropanol, or water-miscible ethers, diethyl ether, tetrahydrofuran, dioxane, or other water-miscible solvent, for example acetonitrile, as inorganic base potassium hydroxide, sodium hydroxide may be applied.

The crystallization is carried out in polar-apolar solvent mixture, preferably in ethyl acetate:hexane mixture and crystallization is repeated several times.

As chiral reagent, optically pure enantiomer of a chiral acid or acid derivative, as malic acid, amino acids, tartaric acid, or tartaric acid derivatives, for example dibenzoyl tartaric acid, camphoric acid or camphoric acid derivatives, for example camphorsulphonic acid, menthyloxyacetic acid, alpha-methoxyphenylacetic acid, alpha-methoxy-alpha-trifluoromethylphenylacetic acid, 2-phenylpropionic acid, mandelic acid or mandelic acid derivatives, for example chloromandelic acid, acetyl-chloromandelic acid, preferably R-acetyl-chloromandelic acid may be applied.

The diastereomers of the general formulae VIa VIb are separated according to the invention by chromatographic method, preferably by atmospheric pressure silica gel chromatography. Chromatography may be carried out applying many-component gradient mixtures as eluents. As the apolar solvent component, saturated hydrocarbon (pentane, hexane, heptane, iso-octane, cyclohexane, methylcyclohexane) or aromatic hydrocarbon (toluene) or halogenated hydrocarbon (dichloromethane) may be applied. As the polar component, alcohol (methanol, ethanol, isopropanol), ester (methyl acetate, ethyl acetate, isopropyl acetate), ether (diethyl ether, methyl tertiary-butyl ether) or ketone-type (acetone, methyl ethyl ketone, methyl isobutyl ketone) solvent mixtures may be applied. As eluent preferably dichloromethane:ethyl acetate mixture may be applied.

According to a preferred embodiment of the invention the optically active Beraprost acid of formula I is isolated in crystalline form. The crystallization is carried out using acetone:water and dichloromethane:diisopropyl ether: hexane solvents. The Beraprost acid of formula I, if desired, is transformed into its salt.

A preferred embodiment of the invention is detailed below:

The starting material of the process is the racemic Beraprost ester (rac-BP-ester, II), which may be prepared according to our patent HU-227158 B1 or patent application WO2003/011849.

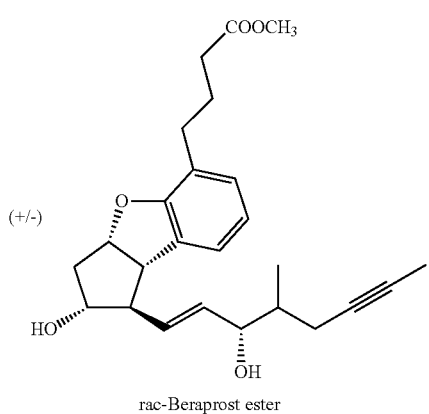

rac-Beraprost ester

The racemic Beraprost ester is the approx. 1:1 ratio mixture of 4 isomers.

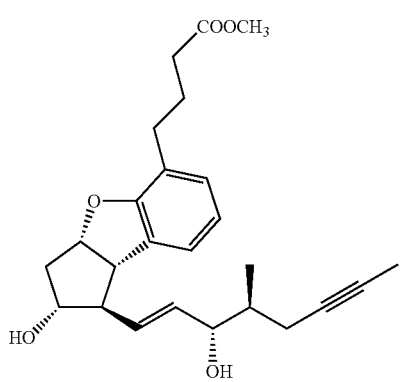

α 2/1

-continued

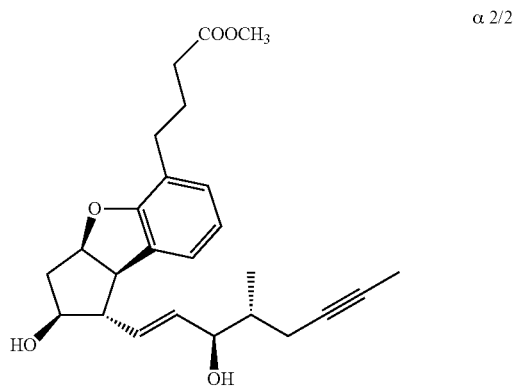

α 2/2

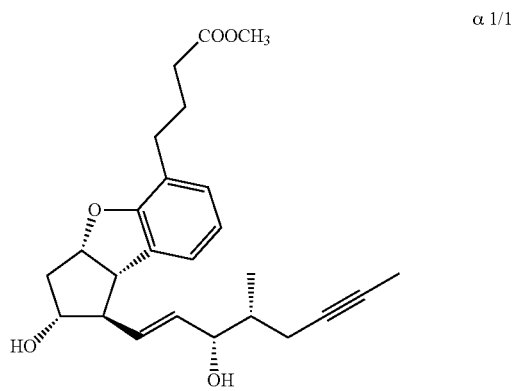

α 1/1

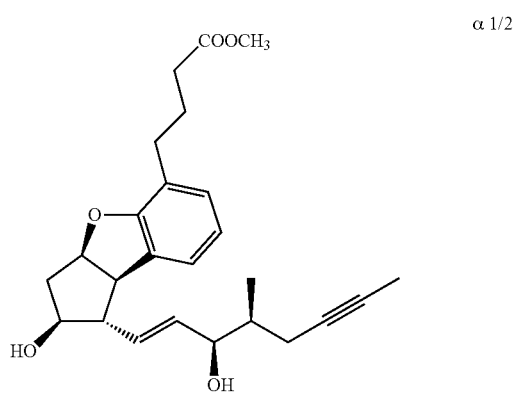

α 1/2

Isomers alpha 2/1-alpha 2/2, and alpha 1/1-alpha 1/2 are enantiomers, whereas isomers alpha 2/1-alpha 1/1, and alpha 2/2-alpha 1/2 are diastereomers.

The basis of our process is that the diastereomers which have different physical characteristics, may be separated by physical methods (e.g. crystallization, chromatography).

Physical characteristics of the enantiomers are, however, identical, the only difference is that they rotate the plane of the linearly polarized light in opposite direction.

Separation of the enantiomers by simple physical methods is not possible, for their separation chiral auxiliary material is needed.

In our process first we separate the diastereomer pairs.

For this purpose the racemic Beraprost ester (II) containing 4 isomers is hydrolyzed into the racemic Beraprost acid (II) containing 4 isomers.

The diastereomers of Beraprost acid are separated by repeated crystallizations. The crystallization is performed from hexane:ethyl acetate solvent mixtures.

After repeated crystallizations the racemic Beraprost acid contains only the alpha 2/1 Beraprost acid and its alpha 2/2 enantiomer.

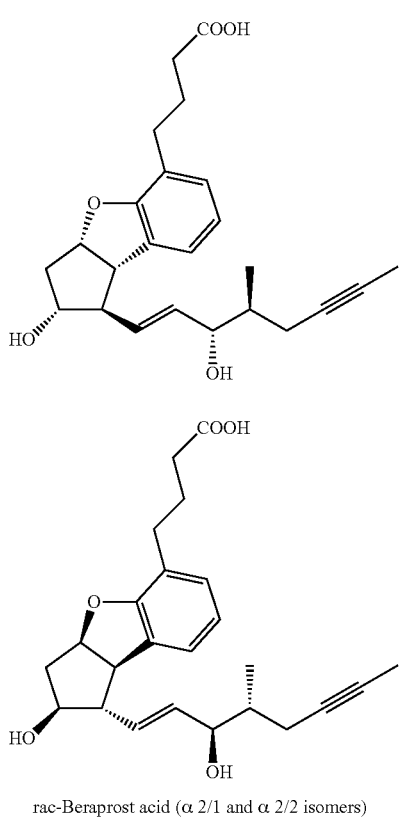

rac-Beraprost acid (α 2/1 and α 2/2 isomers)

Since separation of the enantiomers requires chiral auxiliary material, the rac-Beraprost acid containing the alpha 2/1 and alpha 2/2 enantiomer pair is first esterified with methyl iodide, then the free hydroxyl groups of the rac-Beraprost ester (α 2/1 and α 2/2 isomers) are esterified with chiral acid, R-acetyl-chloromandelic acid (V).

The diacyl-Beraprost ester diastereomers, esterified with chiral acid, may already be separated by physical methods, in our case by chromatography.

The chromatographic separation is performed using dichloromethane: ethyl acetate solvent mixtures.

The main fraction of the chromatography is the diester (diacyl-Beraprost ester (α 2/1)) formed from the active Beraprost ester (IVa) with R-acetyl-chloromandelic acid.

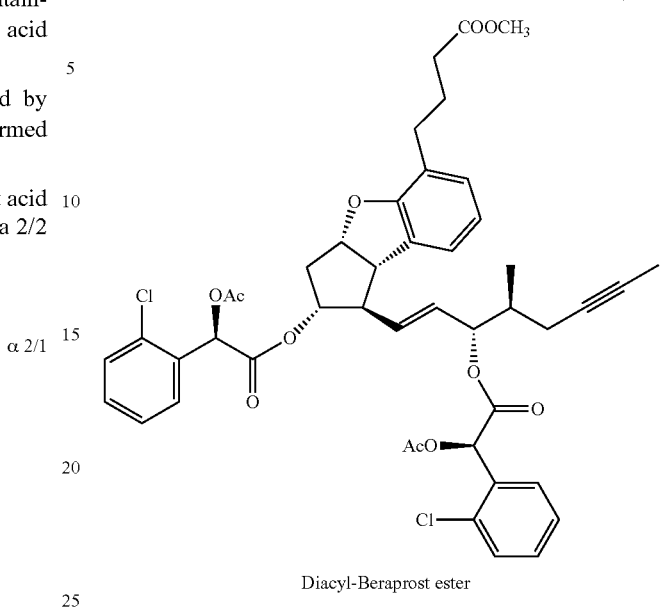

Diacyl-Beraprost ester

Hydrolysis of the ester groups resulted the active Beraprost acid (Beraprost acid (α 2/1), I). The amount of isomeric impurities of the crystalline, active Beraprost acid may be decreased by repeated crystallizations to a value satisfying the limits determined by quality requirements.

Crystallization is carried out from acetone-water and dichloromethane:diisopropyl ether:hexane mixtures.

The active, crystalline Beraprost acid, if desired, may be transformed into its salt.

The process is demonstrated in Schema 8.

Schema 8.

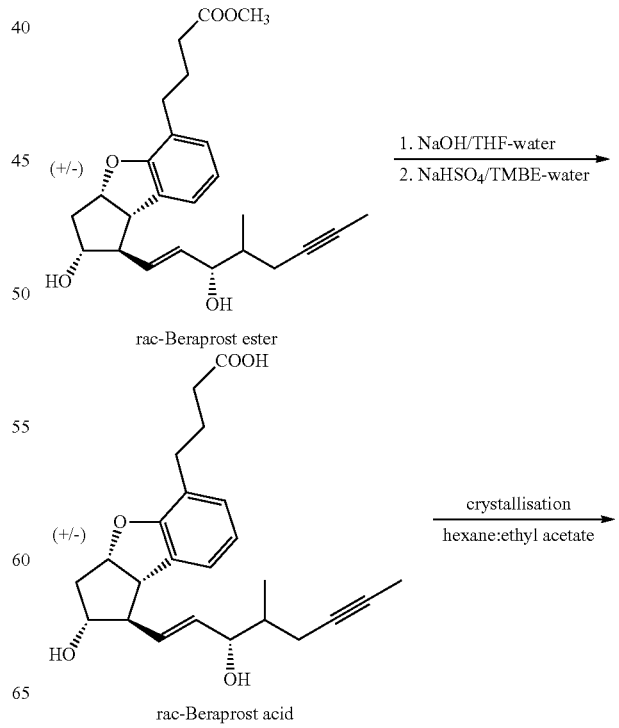

-continued

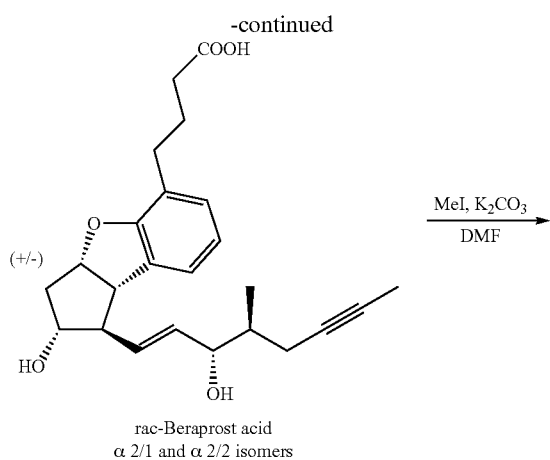

rac-Beraprost acid
α 2/1 and α 2/2 isomers

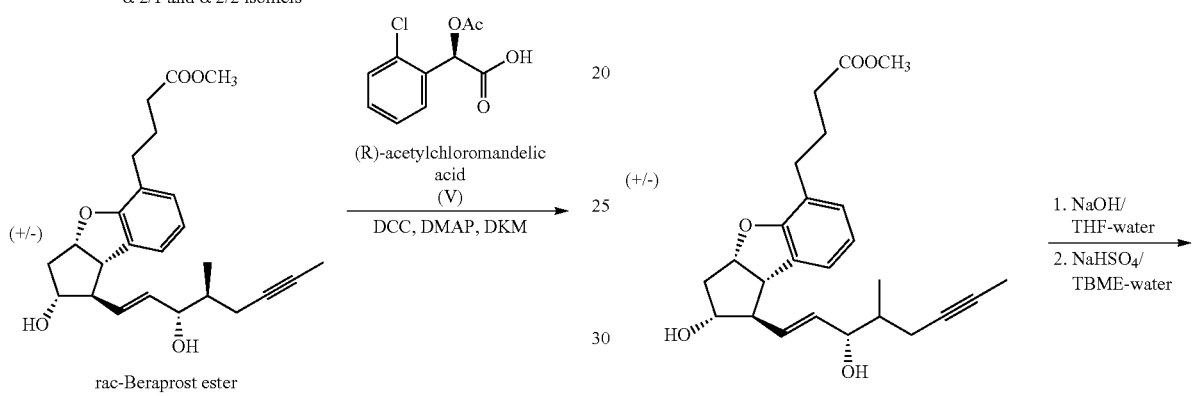

rac-Beraprost ester
α 2/1 and α 2/2 isomers

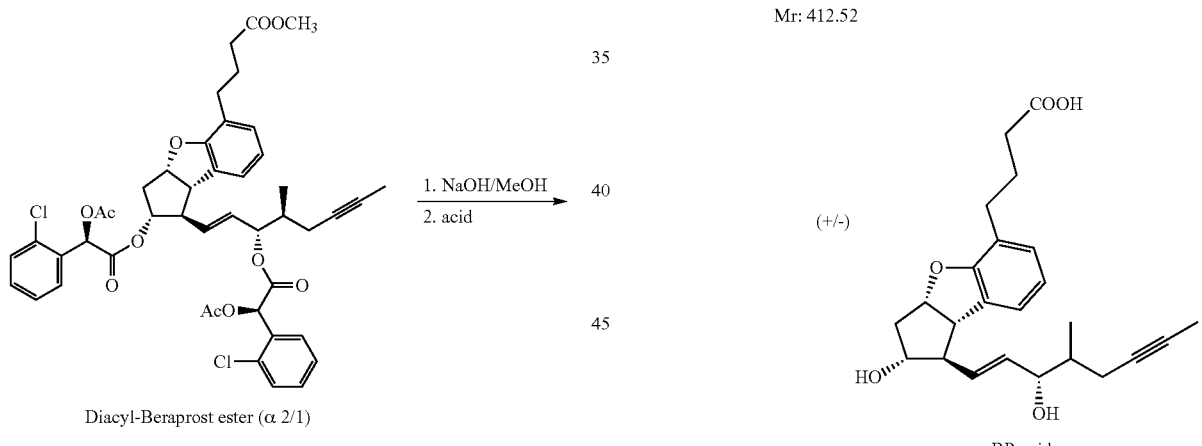

Diacyl-Beraprost ester (α 2/1)

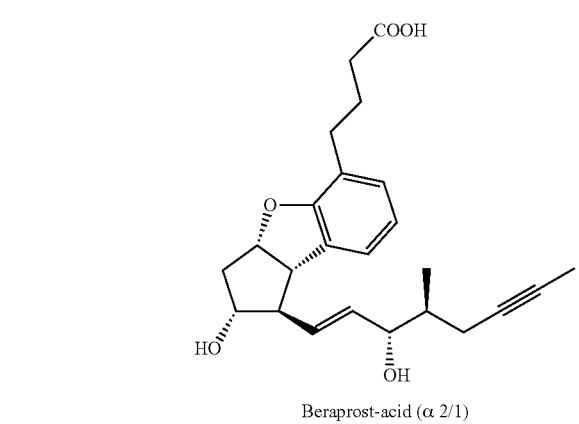

Beraprost-acid (α 2/1)

Our invention is illustrated through the examples below, without limiting what we claim to the solutions described in the examples.

EXAMPLES

Preparation of the Active Beraprost Na (1 α2/1) from Racemic Beraprost Ester (Rac-BP-Ester)

a.) Rac-Beraprost Acid (1R*,2R*,3aS*,8bS*)-2,3,3a,8b-tetrahydro-2-hydroxy-1-[(E,3S*,4RS)-3-hydroxy-4-methyl-1-octen-6-ynyl]-1H-cyclopenta[b]benzofuran-5-butanoic Acid rac-BP-acid
Mr: 412.52 rac-BP-acid
Mr: 398.9

400.0 g of rac-BP-ester is dissolved in 1.5 L of tetrahydrofuran, to the solution at room temperature, in an inert atmosphere, under agitation 6 L of 0.5M sodium hydroxide solution is added. At the end of the hydrolysis the reaction mixture is diluted with water and washed with methyl tert-butyl ether. The aqueous solution is acidified to pH≤3 with 1M sodium hydrogen sulfate solution. The acidic aqueous solution is extracted with methyl tert-butyl ether. The united organic phase is washed to neutral with saturated salt solution, dried over sodium sulfate and evaporated. The evaporated concentrate is dissolved in ethyl acetate and crystallized with hexane.

Yield: 290.0 g (75%).

b.) Rac-Beraprost Acid (α 2/1 and α 2/2 Isomers) (Rac-BP-Acid (α 2/1 and α 2/2 Isomers))

(1R*,2R*,3aS*,8bS*)-2,3,3a,8b-tetrahydro-2-hydroxy-1-[(E,3S*,4S*)-3-hydroxy-4-methyl-1-octen-6-ynyl]-1H-cyclopenta[b]benzofuran-5-butanoic Acid c.) Rac-Beraprost Ester (α 2/1 and α 2/2 Isomers) (Rac-BP-Ester (α 2/1 and α 2/2 Isomers))

(1R*,2R*,3aS*,8bS*)-2,3,3a,8b-tetrahydro-2-hydroxy-1-[(E,3S*,4S*)-3-hydroxy-4-methyl-1-octen-6-ynyl]-1H-cyclopenta[b]benzofuran-5-butanoic Acid Methyl Ester

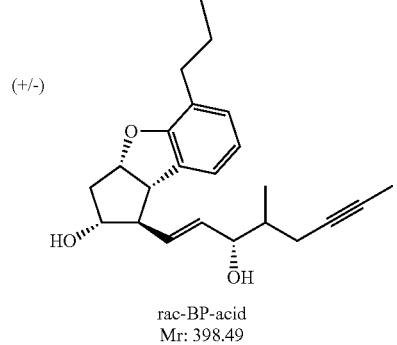

rac-BP-acid
Mr: 398.49 crystallisation
hexane:
ethyl acetate

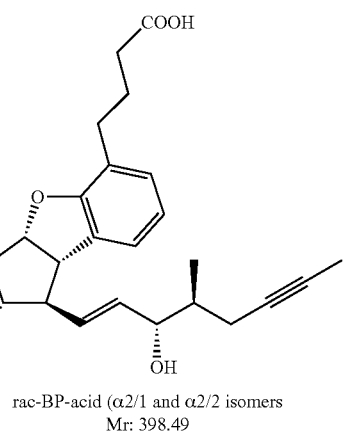

rac-BP-acid (α2/1 and α2/2 isomers
Mr: 398.49

MeI, K₂CO₃
DMF

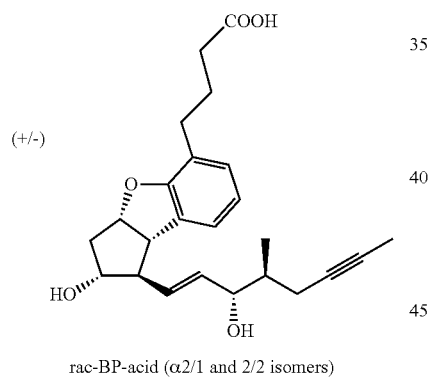

rac-BP-acid (α2/1 and 2/2 isomers)
Mr: 398.49

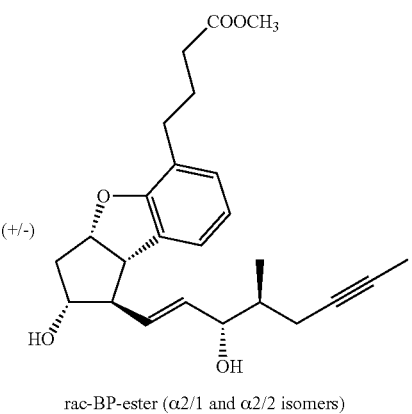

rac-BP-ester (α2/1 and α2/2 isomers)
Mr: 412.52

290 g of rac-BP-acid is dissolved at 50° C. in 2.9 L of ethyl acetate, the solution is cooled to room temperature and under agitation 2.9 L of hexane is added to it. After precipitation of a great amount of crystals, further 1.45 L of hexane is added to the suspension, then it is cooled to 0-10° C. and agitated at that temperature for 15 minutes. The crystals are filtered off and washed.

The filter-wet crystals are crystallized again.

Crystallization is repeated until the amount of the rac-Beraprost acid (α1/1 and α1/2 isomers) decreases to ≤0.5%, as determined by HPLC.

To fulfill the demanded quality requirement 10 crystallizations are needed.

Yield: 82.0 g (28.3%).

82 g of rac-BP-acid (2/1 and 2/2 isomers) is dissolved in 410 mL of dimethylformamide, 49.8 g of potassium carbonate and 25.6 mL of methyl iodide are added to it. The mixture is agitated at 40° C. till reaching the desired conversion. When the reaction has completed the mixture is poured onto acidic water and the product is extracted with toluene. The united organic phase is washed with 1M sodium hydrogen carbonate solution, with water and with saturated salt solution, dried over sodium sulfate and evaporated.

Yield: 84.0 g (99.0%).

D.) Diacyl-Beraprost Ester (α 2/1 Isomer) (Diacyl-BP-Ester (α 2/1))

(1R,2R,3aS,8bS)-2,3,3a,8b-tetrahydro-2-[2R-acetoxy-2-(2-chlorophenyl)-acetoxy]-1-[(E,3S,4S)-3-[2R-acetoxy-2-(2-chlorophenyl)-acetoxy]-4-methyl-1-octen-6-ynyl]-1H-cyclopenta[b]benzofuran-5-butanoic Acid Methyl Ester

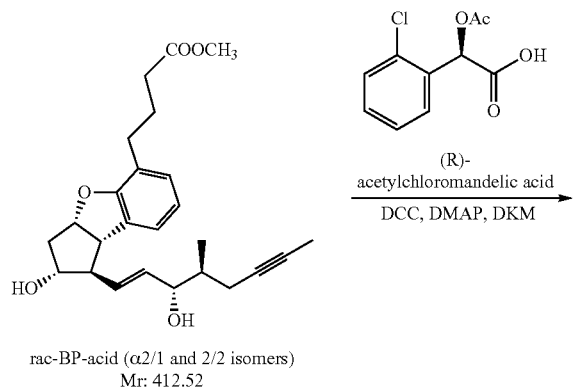

rac-BP-acid (α2/1 and 2/2 isomers)
Mr: 412.52

(R)-acetylchloromandelic acid
DCC, DMAP, DKM

Diacyl-BP-ester (α2/1)
Mr: 833.75

+

Diacyl-BP-ester (α2/2)
Mr: 833.75

84.0 g of rac-BP-ester (α2/1 and α2/2 isomers) is dissolved in an inert atmosphere in 1.68 L of dichloromethane (DCM), to the solution are added 9.95 g of dimethylamin-opyridine (DMAP) and 107.1 g of R-acetylchloromandelic acid, and the mixture is agitated till dissolution. After full dissolution the reaction mixture is cooled to (−)−10° C. and 100.8 g of dicyclohexylcarbodiimide (DCC) is added. The reaction mixture is agitated without cooling till reaching the desired conversion. At the end of the reaction the excess of dicyclohexylcarbodiimide is destroyed with 1M hydrochloric acid, the precipitated material is filtered off and washed with ethyl acetate. The united organic phase is washed with 1M sodium hydrogen carbonate solution, then with saturated salt solution, dried over sodium sulfate and evaporated. The evaporated concentrate is chromatographed on silica gel column using dichloromethane:ethyl acetate=20:1 and dichloromethane:ethyl acetate=5:1 eluent mixtures. The diacyl-BP-ester (α 2/1) isomer eluates after the diacyl-BP-ester (α 2/2) isomer. The main fraction which contains the diacyl-BP-ester (α 2/1) isomer is evaporated.

Yield: 83.0 g (48.9%).

Preparation of R-Acetyl-Chloromandelic Acid

2R-Acetoxy-2-(2-chlorophenyl)acetic Acid

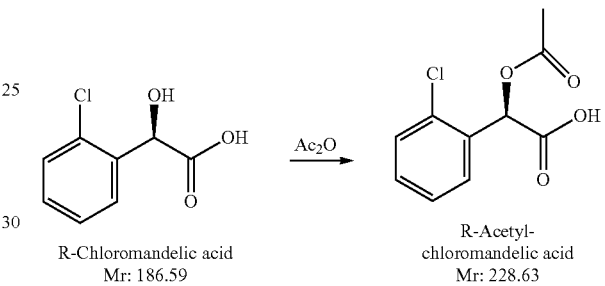

R-Chloromandelic acid
Mr: 186.59

R-Acetyl-chloromandelic acid
Mr: 228.63

100 g of R-Chloromandelic acid is dissolved under agitation at room temperature in 95 mL of acetic anhydride. After full dissolution the reaction mixture is concentrated in vacuum, toluene is added to the concentrate, and toluene is then distilled off in vacuum.

The evaporated concentrate is dissolved in the mixture of diisopropyl ether and hexane at room temperature. The solution is agitated till crystallization starts, then further amount of hexane is added. The suspension is cooled to 0° C. to complete the crystallization.

Yield: 112.0 g (91.4%).

e.) Beraprost Acid (α 2/1 Isomer) (BP-Acid (α 2/1)

(1R,2R,3aS,8bS)-2,3,3a,8b-tetrahydro-2-hydroxy-1-[(E,3S,4S)-3-hydroxy-4-methyl-1-octen-6-ynyl]-1H-cyclopenta[b]benzofuran-5-butanoic Acid

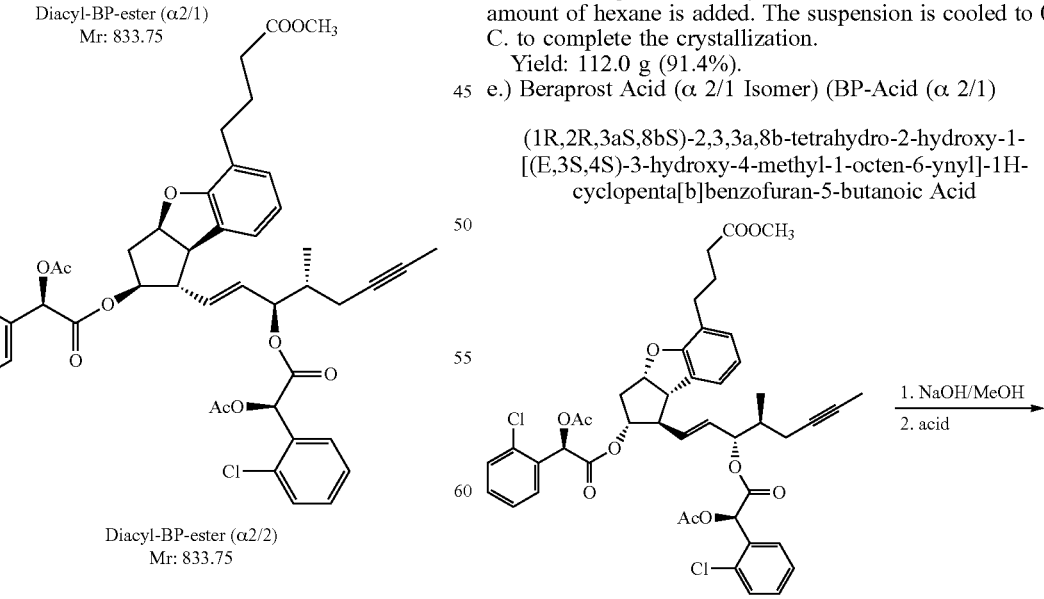

Diacyl-BP-ester (α2/1)
Mr: 833.75

1. NaOH/MeOH
2. acid

-continued

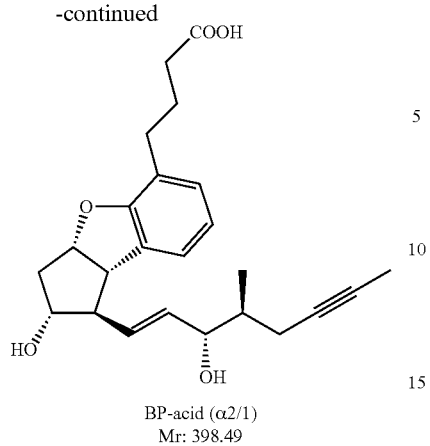

BP-acid (α2/1)
Mr: 398.49

83.0 g of diacyl-BP-ester (α2/1) is dissolved in 1 L of methanol. To the solution 0.84 L of 1M sodium hydroxide solution is added and the mixture is agitated until hydrolysis proceeds. At the end of the reaction methanol is removed in vacuum. The concentrated solution is acidified with 1M sodium hydrogen sulfate solution and extracted with ethyl acetate. The united organic phase is washed with saturated salt solution, dried over sodium sulfate and evaporated.

The evaporated concentrate is dissolved in 256 mL of acetone and crystallized at room temperature with 2.57 L of water. The crystals are filtered off and the filter-wet product is repeatedly dissolved at 35-40° C. in 143 mL of acetone and after cooling to room temperature crystallized with 1.43 L of water. The crystals are filtered off and dried.

The dry crystals are suspended at 40° C. in the mixture of 70 mL of dichloromethane and 525 mL of diisopropyl ether, agitated for 10 minutes and cooled slowly to 25° C. The undissolved crystals are filtered off.

To the filtrate solution approx. 1 L of hexane is added dropwise at room temperature, the crystal suspension is then cooled to 0° C. to complete the crystallization. The crystals are filtered off, washed and dried.

Yield: 30.0 g, (75.6%), melting point: 61-64° C.

Characteristic peaks of the X-ray diffraction spectrum (shown in FIG. 1.) of the crystalline optically active Beraprost acid:

| °2Theta | relative intensity (%) |
|---------|------------------------|
| 6.1532  | 100.00                 |
| 7.1324  | 51.49                  |
| 12.2637 | 94.90                  |
| 16.0125 | 82.22                  |
| 19.1605 | 61.64                  |
| 19.3288 | 82.45                  |
| 19.4872 | 53.29                  |

Measurement conditions of the X-ray diffraction spectrum:
Start position [° 2Theta]: 2.0084
End position [° 2Theta]: 39.9864
Measurement temperature [° C.]: 25.00
Anode material: Cu
K-Alpha1 [L]: 1.54060
K-Alpha2 [L]: 1.54443
DCS curve of the above material is shown in FIG. 1.
DSC measurement conditions:
Instrument:
METTLER TOLEDO DSC1 STAR$^e$ System
Star$^e$ basic V9.30

Method:
Starting temperature: 150° C.
End temperature: 250° C.
Heating speed: 10° C./min, 5° C./min, 2° C./min
Weight: 2-6 mg
Perforated alumina pot (40 μl)

The invention claimed is:
1. Process for the preparation of the optically active Beraprost of formula I and its salts

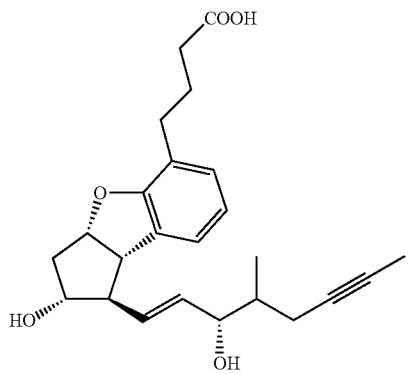

comprising:
a.) hydrolyzing a racemic Beraprost ester of the general formula II,

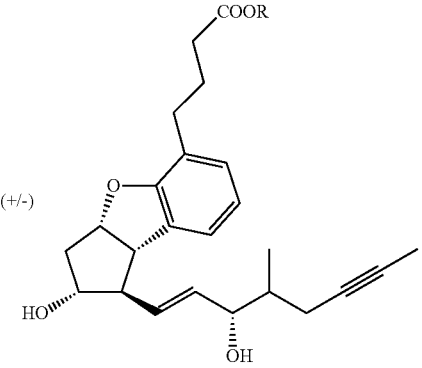

where R is a $C_{1-4}$ straight- or branched-chain alkyl group, crystallizing the resulting racemic Beraprost acid of formula III

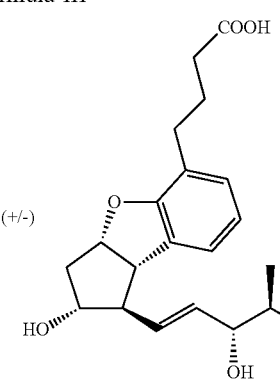

esterifying the obtained Beraprost acid enantiomers of formula IIIa and IIIb

IIIa
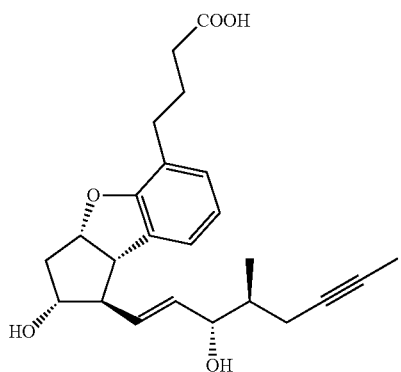

IIIb
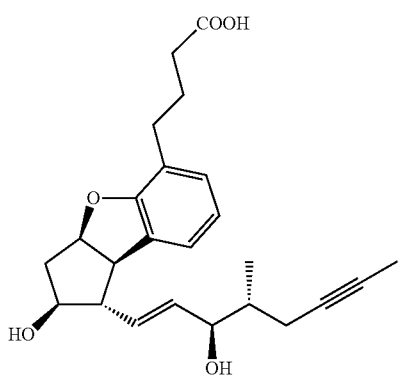

reacting the resulting Beraprost ester enantiomers of formula IVa and IVb,

IVa
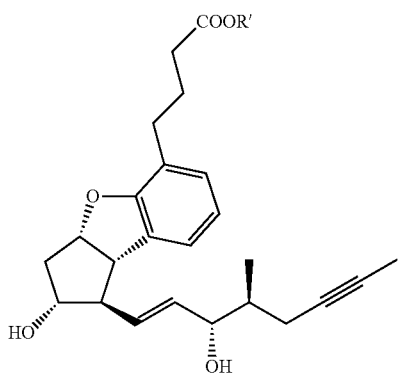

IVb
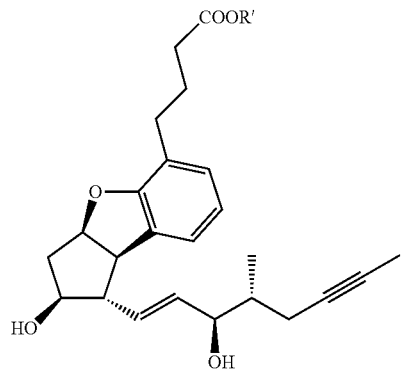

where R' is a $C_{1-4}$ straight- or branched-chain alkyl group with a chiral reagent, separating the obtained diacyl-Beraprost ester diastereomers, VIa and VIb, VIa
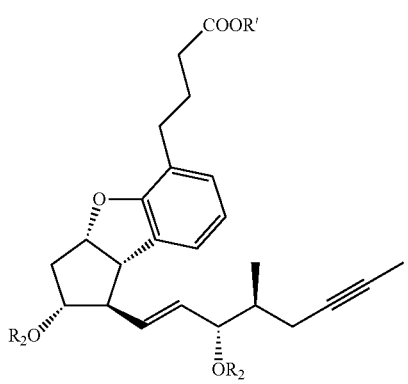

VIb
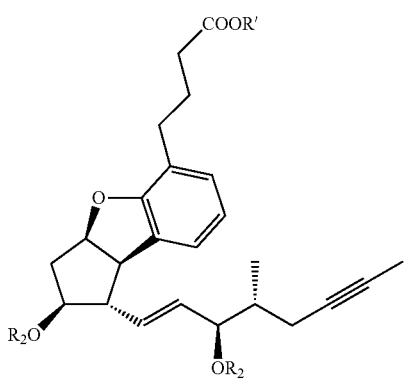

where R' is as defined above and $R^2$ is an acid residue group containing chiral carbon atom, hydrolyzing the Beraprost ester of formula VIa, and crystallizing the obtained optically active Beraprost acid of formula I, and optionally, transforming said optically active Beraprost acid into a salt.

2. The process as defined in claim 1, wherein hydrolysis of the compound of formula II is carried out with the aqueous solution of an inorganic base, in water-miscible organic solvent.

3. The process as defined in claim 2, wherein as organic solvent alcohols, comprising ethanol, isopropanol, or water-miscible ethers, preferably diethyl ether or tetrahydrofuran are applied.

4. The process as defined in claim 2, wherein as inorganic base sodium hydroxide, potassium hydroxide are applied.

5. The process as defined in claim 1, wherein crystallizing is performed in polar-apolar solvent mixture.

6. The process as defined in claim 5, wherein crystallizing is performed using ethyl-acetate: hexane mixture.

7. The process as defined in claim 1, wherein crystallizing is repeated several times.

8. The process as defined in claim 1, wherein as chiral reagent, chiral acid or its derivative is applied.

9. The process as defined in claim 8, wherein as chiral acid optically pure enantiomers of malic acid, amino acids or tartaric acid or tartaric acid derivatives, camphoric acid or camphoric acid derivatives, menthyloxyacetic acid, alpha-methoxyphenylacetic acid, alpha-methoxy-alpha-trifluoromethylphenylacetic acid, 2-phenylpropionic acid, mandelic acid or mandelic acid derivatives, preferably R-configuration acetyl-chloromandelic acid may be applied.

10. The process as defined in claim 1, wherein the diastereomers of the general formula VIa and VIb are separated by chromatographic method.

11. The process as defined in claim 10, wherein atmospheric pressure silica gel chromatography is applied.

12. The process as defined in claim 10, wherein chromatography is carried out applying multi-component gradient eluent.

13. The process as defined in claim 12, wherein as eluent, a mixture containing apolar and polar components, preferably dichloromethane: ethyl acetate mixture is applied.

14. The process as defined in claim 1, wherein the optically active Beraprost acid of formula I is isolated in crystalline form.

15. The process as defined in claim 14, wherein the optically active Beraprost acid of formula I is crystallized with acetone:water and dichloromethane:diisopropyl ether: hexane solvents.

16. The process as defined in claim 14, wherein the melting point of the optically active Beraprost acid of formula I prepared by the method is 61-64° C.

17. The process as defined in claim 14, wherein the characteristic peaks of the X-ray diffraction spectrum of the optically active Beraprost acid of formula I prepared by the method are:

| °2Theta | relative intensity (%) |
|---------|------------------------|
| 6.1532  | 100.00                 |
| 7.1324  | 51.49                  |
| 12.2637 | 94.90                  |
| 16.0125 | 82.22                  |
| 19.1605 | 61.64                  |
| 19.3288 | 82.45                  |
| 19.4872 | 53.29.                 |

* * * * *